(12) United States Patent
Graybill et al.

(10) Patent No.: US 7,311,522 B2
(45) Date of Patent: Dec. 25, 2007

(54) ENDODONTIC INSTRUMENTS AND METHOD OF MANUFACTURING SAME

(75) Inventors: Lonnie M. Graybill, York, PA (US); Jack L. Shearer, York, PA (US); Jeff Ludwig, York, PA (US)

(73) Assignee: Miltex Technology Corporation, Wilmington, DE (US)

( * ) Notice: Subject to any disclaimer, the term of this patent is extended or adjusted under 35 U.S.C. 154(b) by 533 days.

(21) Appl. No.: 10/963,879

(22) Filed: Oct. 13, 2004

(65) Prior Publication Data
US 2005/0100859 A1 May 12, 2005

Related U.S. Application Data

(63) Continuation-in-part of application No. 10/403,400, filed on Mar. 31, 2003.

(51) Int. Cl.
*A61C 5/02* (2006.01)
(52) U.S. Cl. ...................................... 433/102
(58) Field of Classification Search ................ 433/102, 433/165, 224; 451/48; 205/640, 644
See application file for complete search history.

(56) References Cited

U.S. PATENT DOCUMENTS

| | | | |
|---|---|---|---|
| 444,383 A | 1/1891 | Ivory | |
| 498,554 A | 5/1893 | Johanson | |
| 717,594 A | 1/1903 | Miles, Jr. | |
| 1,067,015 A | 7/1913 | Fowler | |
| 1,307,446 A | 6/1919 | Kerr | |
| 3,832,779 A | 9/1974 | Raynaud | |
| 4,019,254 A | 4/1977 | Malmin | |
| D250,544 S | 12/1978 | Leonard | |

(Continued)

OTHER PUBLICATIONS

Aerospace Industries Association of America; *Reamers, Chucking*: National Aerospace Standard; Aug. 1985; sheets 1-21.

(Continued)

*Primary Examiner*—Melba Bumgarner
(74) *Attorney, Agent, or Firm*—Jones Day

(57) ABSTRACT

A method of manufacturing an endodontic instrument using an electrochemical (ECG) grinding process. An instrument blank is formed from stock material, and an electric current is applied between an electrically conductive grinding wheel, acting as a cathode, and the instrument blank, acting as an anode. A continuous stream of electrolyte fluid, a conductive aqueous solution, is applied at an interface between the grinding wheel and the instrument blank, the electrolyte fluid having an associated volume and pressure. The instrument blank is advanced past the electrically conductive grinding wheel to remove material from the instrument blank to form at least one cutting flute. The electric current applied between the grinding wheel and the instrument blank is reduced, and the instrument blank is advanced past the grinding wheel again to form a finish surface, e.g., a sharp cutting edge, on the at least one cutting flute. The process may be repeated to form an endodontic instrument having a plurality of cutting flutes. The cutting flutes may be helically or non-helically shaped. The instrument blank is formed of an electrically conductive material, such as nickel titanium or stainless steel. In one variation, the electric current may be eliminated entirely during the final finishing pass. The volume and pressure of the electrolyte may be varied. Endodontic instruments formed by the method of the present invention are also disclosed.

41 Claims, 5 Drawing Sheets

U.S. PATENT DOCUMENTS

| | | |
|---|---|---|
| 4,190,958 A | 3/1980 | Martin et al. |
| 4,260,379 A | 4/1981 | Groves et al. |
| 4,299,571 A | 11/1981 | McSpadden |
| 4,332,561 A | 6/1982 | McSpadden |
| 4,353,698 A | 10/1982 | McSpadden |
| 4,443,193 A | 4/1984 | Roane |
| 4,518,356 A | 5/1985 | Green |
| 4,536,159 A | 8/1985 | Roane |
| 4,611,508 A | 9/1986 | Roane |
| 4,661,061 A | 4/1987 | Martin |
| 4,934,934 A | 6/1990 | Arpaio, Jr. et al. |
| 4,990,088 A | 2/1991 | Weissman |
| 4,999,952 A | 3/1991 | Speiser et al. |
| 5,065,549 A | 11/1991 | Speiser et al. |
| 5,417,525 A | 5/1995 | Lenhart |
| 5,464,362 A | 11/1995 | Heath et al. |
| 5,484,327 A | 1/1996 | Kovach |
| 5,527,205 A | 6/1996 | Heath et al. |
| 5,624,259 A | 4/1997 | Heath et al. |
| 5,628,674 A | 5/1997 | Heath et al. |
| 5,653,590 A | 8/1997 | Heath et al. |
| 5,655,950 A | 8/1997 | Heath et al. |
| 5,658,145 A | 8/1997 | Maillefer et al. |
| 5,713,736 A | 2/1998 | Heath et al. |
| 5,746,597 A | 5/1998 | Maillefer et al. |
| 5,762,541 A | 6/1998 | Heath et al. |
| 5,807,106 A | 9/1998 | Heath |
| 5,842,862 A | 12/1998 | Nissan |
| 5,876,202 A | 3/1999 | Berlin |
| 5,882,198 A | 3/1999 | Taylor et al. |
| 5,921,775 A | 7/1999 | Buchanan |
| 5,941,760 A | 8/1999 | Heath et al. |
| 6,012,921 A | 1/2000 | Riitano |
| 6,042,376 A | 3/2000 | Cohen et al. |
| 6,126,521 A | 10/2000 | Shearer |
| 6,139,715 A * | 10/2000 | Wei .............................. 205/652 |
| 6,409,506 B1 | 6/2002 | Graybill |
| 2003/0199236 A1 | 10/2003 | Aloise et al. |

OTHER PUBLICATIONS

NT Company, *The Next Major Leap Forward in Endodontics Is Quantec*; 1996, 6 pages.

Brassler, USA; *Systems for Endodontic Excellence* (advertisement); Dental Products Report, May 2002, p. 13.

*ProTaper Rotary Instruments*; http://store.tulsadental.com/catalog/protaper_desc.htm; May 14, 2002.

*ProFile GT Rotary Instruments*; http://store.tulsadental.com/catalog/profile_gt_rotary_desc.htm; May 14, 2002.

*ProFile .04 and .06 ISO Rotary Instruments*; http://store.tulsadental.com/catalog/profile_04_06_iso_rotary_instruments_desc.htm; May 14, 2002.

*ProFile Series .04 and .06 Rotary Tapers*; http://store.tulsadental.com/catalog/profile_series_04_06_rotary_tapers_desc.htm; May 14, 2002.

FKG Dentaire; *FKG RaCe Rotary Endodontic System*; 7 pages, date not available.

Tycom; *Quantec Endodontic Instrumentation*; 9 pages, date not available.

\* cited by examiner

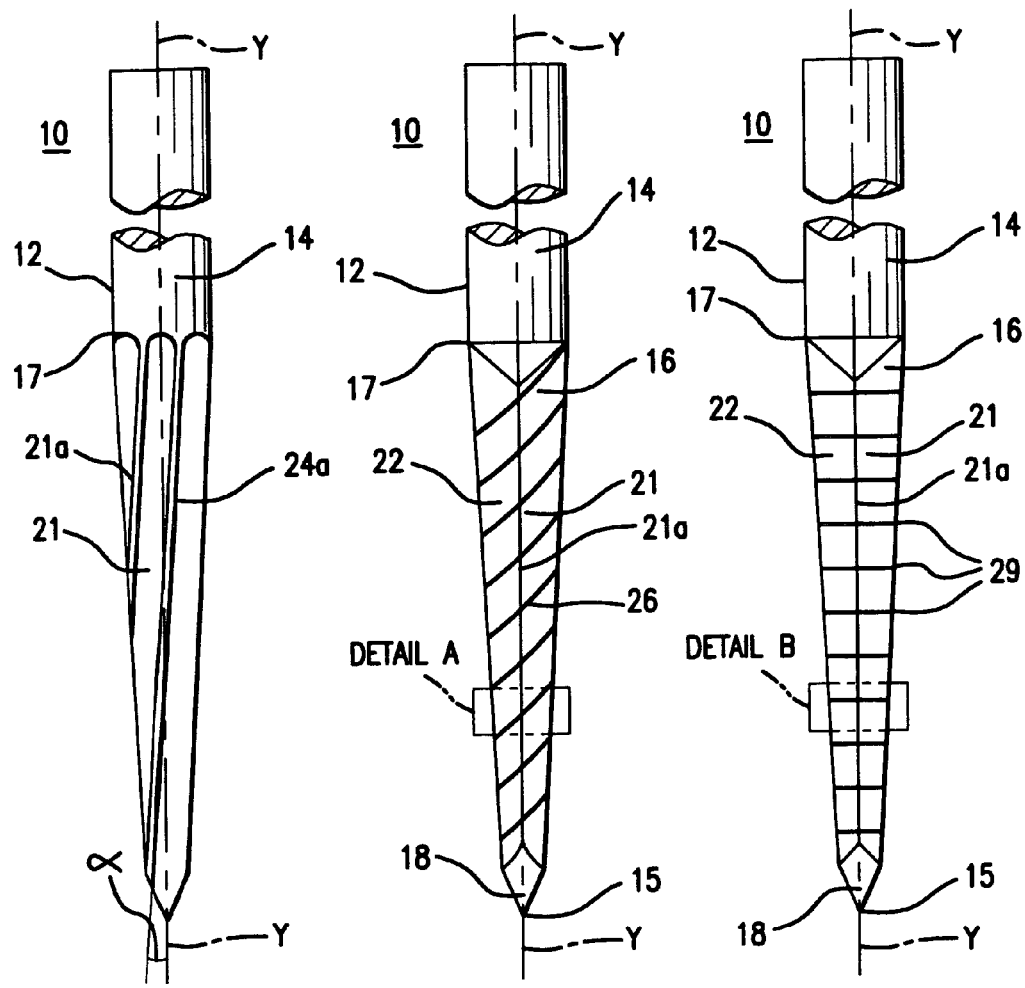
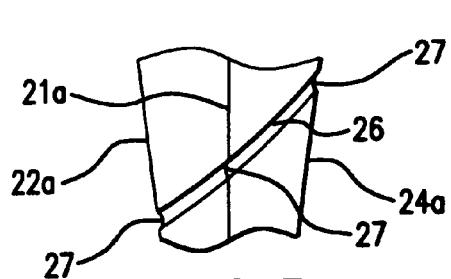
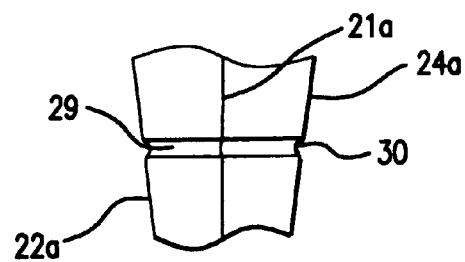
FIG.5   FIG.6   FIG.8
FIG.7   FIG.9

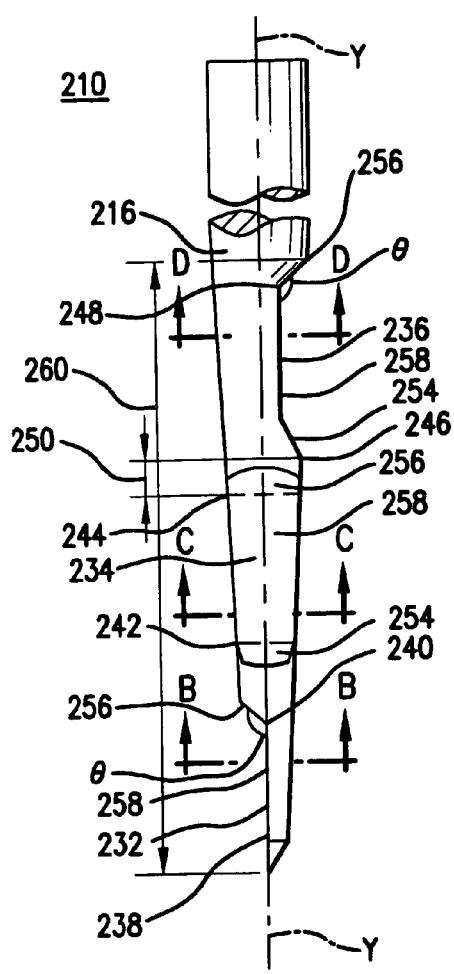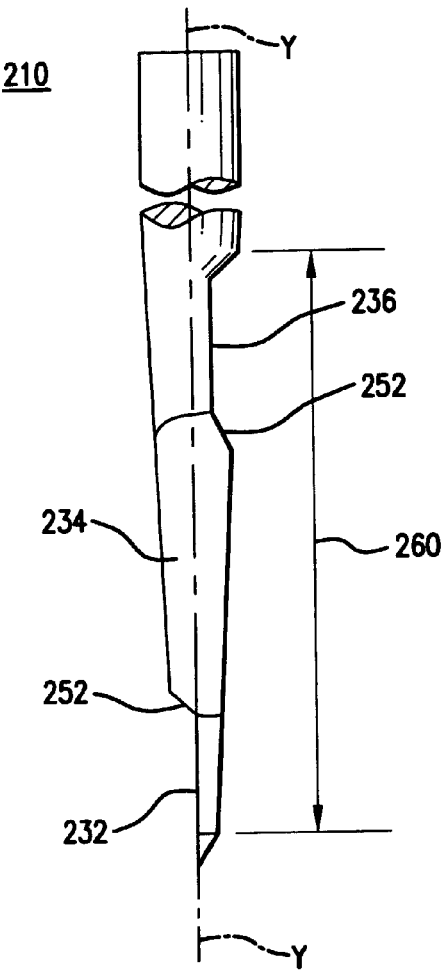
FIG. 10  FIG. 14
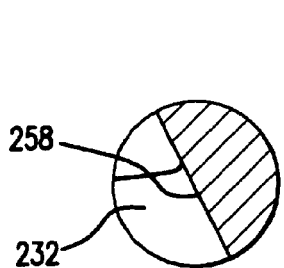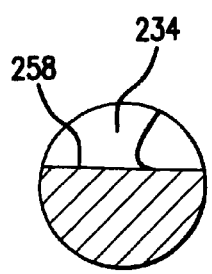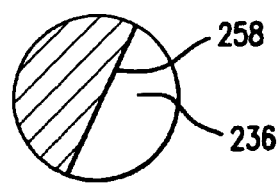
FIG. 11  FIG. 12  FIG. 13

ENDODONTIC INSTRUMENTS AND METHOD OF MANUFACTURING SAME

CROSS REFERENCE TO RELATED APPLICATIONS

The present application is a continuation-in-part of pending U.S. patent application Ser. No. 10/403,400, which was filed on Mar. 31, 2003 and is entitled "Endodontic Instrument."

FIELD OF THE INVENTION

The present invention relates to endodontic instruments and methods of manufacturing endodontic instruments. More particularly, the present invention relates to a method of manufacturing such instruments using an electrochemical grinding (ECG) process.

BACKGROUND OF THE INVENTION

When a tooth decays to the point where the inner nerves and roots become infected, dentists must oftentimes perform a root canal procedure in order to save the tooth and prevent further infection. The primary goal of a root canal is to remove all of the decayed or injured nerve while leaving the integrity of the root canal walls relatively unaffected. Preserving the integrity of the root canal is important in order to allow proper filling of the root canal such that leakage or communication between the root canal system and the surrounding and supporting tissues of the tooth is prevented.

To perform a root canal procedure, the endodontist first drills into the tooth to locate the root canal. Endodontic instruments, commonly referred to as files and reamers, are then used to clean and enlarge the root canals of the tooth. The purpose of the cleaning and enlarging procedure is to remove dead, decayed, or infected tissue from the root canals and to enlarge the root canals so that they can be filled. The reamers and files can either be finger manipulated or engine driven by the endodontist, e.g., rotary, oscillating, reciprocating, etc., and are typically of small diameter to allow them to be used in the small working environment of the root canal.

Endodontic files and reamers may employ helical flutes, as shown in U.S. Pat. No. 6,409,506 to Graybill, or non-helical flutes, as disclosed in related U.S. patent application Ser. No. 10/403,400. The build-up of debris between the flutes of the instrument and the canal walls can cause damage to the canal walls and/or lead to failure of the instrument. Therefore, during the root canal procedure it is important to evacuate the debris adequately as the file or reamer enlarges the root canal and progresses toward its apex.

One problem associated with helical fluted endodontic instruments involves the instrument self-threading or screwing into the canal. This is because helical flutes have continuous helically oriented cutting edges that dig in and thread or screw into the canal. This self-threading propensity of helically fluted instruments is a major undesirable operational characteristic that is a leading cause of instrument breakage. Many modifications of helical fluted instruments have been employed to address this drawback. Some of these modifications include varying the helical angles, varying the pitch, radial lands, and passive rake angles. In other instances, the taper of such instruments has been increased from a standard 0.02 mm:mm taper in an effort to enlarge the cross-sectional area, and increase the strength of the instrument to minimize breakage. Non-helically, or straight, fluted instruments have also been developed to address many of these issues.

Traditionally, endodontic instruments, regardless of the material of manufacture, have been manufactured by one of two fundamental methods. In one method an appropriate size blank of the desired material has a portion of its length ground into a desired cross sectional shape (i.e. square, triangular, rhomboid, etc.), taper (i.e. 0.02 mm:mm, 04 mm:mm etc.) and size. Next the ground portion of the blank is twisted by pulling the ground cross section through a set of gripping jaws while the blank is twisted at a prescribed rate. The result is the formation of an endodontic instrument with helical cutting flutes.

In the second method, an appropriate size blank of the desired material has a helical flute form of desired cross section and taper ground directly into a portion of its length. This is generally accomplished by rotating the blank of material as it passes axially one or more times past a rotating grinding wheel of proper form that is simultaneously translated perpendicular to the axis of the blank. In some variations of this method, the blank having helical flutes ground into it is pre-tapered prior to the fluting process.

In both these traditional methods, a grinding wheel of a chosen size, shape and composition running at an appropriate speed and feed with proper cutting oil type, volume, and pressure is employed to remove material from the blank to create the desired size and taper in the fluted cutting portion of the instrument. As explained in the first method, noted above, a further twisting process is commonly employed to create a helical fluted instrument when utilizing that method. However as disclosed in U.S. patent application Ser. No. 10/403,400, non-helical flute forms can also be employed successfully in endodontic instruments and are sometimes functionally superior to helical flute forms, especially in engine driven rotary applications.

In both of the methods described above, only mechanical abrasion is used to form the taper and cutting flutes of the instrument. Consequently, a substantial amount of heat is generated, and the instrument may experience mechanical stresses, burrs and other distortions. In addition, grinding wheels used for such machining must be dressed and/or replaced frequently. Another electrical discharge machining process disclosed in US 2003/0199236 A1 involves the removal and redepositing of at least a portion of the material removed on the instrument blank to form a recast layer having a second hardness of at least about 15% greater than the original hardness of the base material, thereby altering the mechanical properties of the material.

Therefore, there is a need for a method of manufacturing an endodontic instrument that removes material from an instrument blank in a rapid and precise manner, free from excessive heat, mechanical stress, burrs and other dimensional distortions, while also preserving the mechanical properties, i.e., hardness, of the original base material.

SUMMARY OF THE INVENTION

In a preferred embodiment, the present invention relates to a method of manufacturing endodontic instruments having helical or non-helical flutes, or flutes of other varying configurations. In this method, the material blank is positioned, oriented, and translated with respect to a grinding wheel in the same manner as commonly employed in the two traditional machining methods discussed above. However, the present invention employs an electrochemical grinding (ECG) process, which utilizes a combination of electrical energy, chemical energy and mechanical abrasion to remove material in a rapid and precise manner, free of heat, stress, burrs and mechanical distortions. Unlike the electrical discharge machining and related processes disclosed in US2003/0199236A1 noted above, in the present invention, removed material is not redeposited on the instrument blank to form a recast layer having a second hardness of at least about 15% greater than the first hardness. In fact the new ECG process induces no heat or mechanical stress into the work piece and has no impact on the mechanical properties or hardness (surface or otherwise) of the instrument blank being ground.

In a preferred embodiment, the present invention relates to a method of manufacturing an endodontic instrument comprising the steps of: (a) forming an instrument blank from stock material; (b) applying an electric current between an electrically conductive grinding wheel, acting as a cathode, and the instrument blank, acting as an anode; (c) applying a stream of electrolyte fluid at an interface between the grinding wheel and the instrument blank, the electrolyte fluid having an associated volume and pressure; (d) advancing the instrument blank past the electrically conductive grinding wheel to remove material from the instrument blank to form at least one cutting flute; (e) reducing the electric current applied between the grinding wheel and the instrument blank; and (f) repeating step (d) to form a finish surface on the at least one cutting flute. The cutting flutes may be helically or non-helically shaped. In one variation, in step (e) the current may be eliminated entirely. The instrument blank may be formed of an electrically conductive material, such as nickel titanium or stainless steel.

The volume, pressure and concentration of the conductive electrolyte fluid, which may include a salt, such as sodium chloride, and other additives may be varied. In one embodiment, the instrument blank is rotated and steps (b) through (f), above, are repeated to form a plurality of cutting flutes having sharp edges on the instrument blank, and material may also be removed from the instrument blank to form one or more tapered portions.

In another preferred embodiment, the present invention relates to an endodontic instrument for use in performing root canal therapy on a tooth comprising at least one cutting flute, the cutting flute formed by the steps of: (a) applying an electric current between an electrically conductive grinding wheel, acting as a cathode, and an instrument blank, acting as an anode; (b) applying a stream of electrolyte fluid at an interface between the grinding wheel and the instrument blank, the electrolyte fluid having an associated volume and pressure; (c) advancing the instrument blank past the electrically conductive grinding wheel to remove material from the instrument blank to form the at least one cutting flute; (d) reducing the electric current applied between the grinding wheel and the instrument blank; and (e) repeating step (d) to form a finish surface on the at least one cutting flute. The instrument may be formed of any suitable electrically conductive material, and may include one or more helical and/or non-helical cutting flutes with sharp edges.

In other preferred aspects, the present invention relates to an endodontic instrument having a longitudinal central axis, a shank portion and an elongated working portion extending from the shank portion along the central axis. The elongated working portion has a proximal end, a distal end, and at least one peripheral surface. At least one straight flute is formed on at least a portion of the peripheral surface of the working portion, the straight flute forming at least one cutting edge on the peripheral surface. The working portion of the instrument may be non-tapered or either uniformly or non-uniformly tapered. The straight flute may be substantially parallel to the central axis, and the cutting edge may have a negative rake angle, a neutral angle, or a positive rake angle. In an alternate preferred embodiment, the straight flute and/or the cutting edge may be oriented at an angle $\alpha$ with respect to the central axis. In still another preferred embodiment, the instrument may further comprise at least one helical flute formed on the peripheral surface of the working portion adjacent the at least one straight flute.

The at least one straight flute may comprise a plurality of flute sections disposed on the peripheral surface of the instrument, the plurality of flute sections angularly displaced about the central axis with respect to one another and each flute section having first and second ends defined along the central axis. In one preferred aspect, a first end of a first flute section is disposed along the longitudinal central axis between the first and second ends of a second flute section such that the first and second flute sections overlap longitudinally along the central axis. A gate may be formed where the first and second flute sections overlap longitudinally to facilitating evacuation of cutting debris up the flute. The plurality of flute sections may each further comprise first and second end surfaces with an intermediate surface disposed therebetween, the end surfaces each disposed in a plane transverse to the intermediate surface. The at least one end surface may be generally perpendicular to the intermediate surface, or, alternatively, may be disposed at an angle $\theta$ greater than 90° from the intermediate surface.

In another preferred embodiment, the second end of one of the flute sections is substantially adjacent the first end of another of the flute sections. In still another preferred embodiment, a non-fluted intermediate section is disposed between the at least two flute sections. In yet another preferred embodiment, the cutting edge includes at least one notch, which may be provided by a helical groove formed along at least a portion of the working portion or at least one circular or circumferential groove formed along at least a portion of the working portion.

BRIEF DESCRIPTION OF THE DRAWINGS

FIG. 5 is a side elevational view of another exemplary instrument according to the present invention;

FIG. 6 is a side elevational view of another exemplary instrument according to the present invention;

FIG. 7 is an enlarged elevational view of "Detail A" shown in FIG. 6;

FIG. 8 is a side elevational view of an exemplary instrument according to the present invention;

FIG. 9 is an enlarged elevational view of "Detail B" shown in FIG. 8;

FIG. 10 is a side elevational view of another exemplary instrument according to the present invention;

FIG. 11 is an enlarged cross-sectional view of the instrument taken along line B-B of FIG. 10;

FIG. 12 is an enlarged cross-sectional view of the instrument taken along line C-C of FIG. 10;

FIG. 13 is an enlarged cross-sectional view of the instrument taken along line D-D of FIG. 10;

FIG. 14 is a side elevational view of another exemplary instrument according to the present invention;

DETAILED DESCRIPTION OF THE PREFERRED EMBODIMENTS

The present invention relates to an improved endodontic instrument for use in performing root canal therapy on a tooth. In practice, endodontic files and reamers, whether finger manipulated or engine driven, are not normally used in a traditional drill or reamer like fashion. More specifically, endodontic files and reamers are not commonly used in a manner where the instrument is continually rotated in one direction and advanced continuously forward. In reality, finger manipulated files and reamers are quite often used in a watch-winding, quarter-turn-and-pull, or hybrid-balance-force fashion. Engine driven rotary techniques commonly use peck-drill motions, which advance the file or reamer incrementally forward and then retract the instrument. Furthermore, both finger manipulated and engine driven techniques also include repeatedly retracting the file or reamer from the canal to allow irrigation and the introduction of lubricants, which enables debris to be evacuated. Moreover, all root canal techniques use multiple files or reamers of different sizes and tapers and the repeated changing of files or reamers inherently provides a mechanism to remove accumulated debris from the canal.

Figure 1:
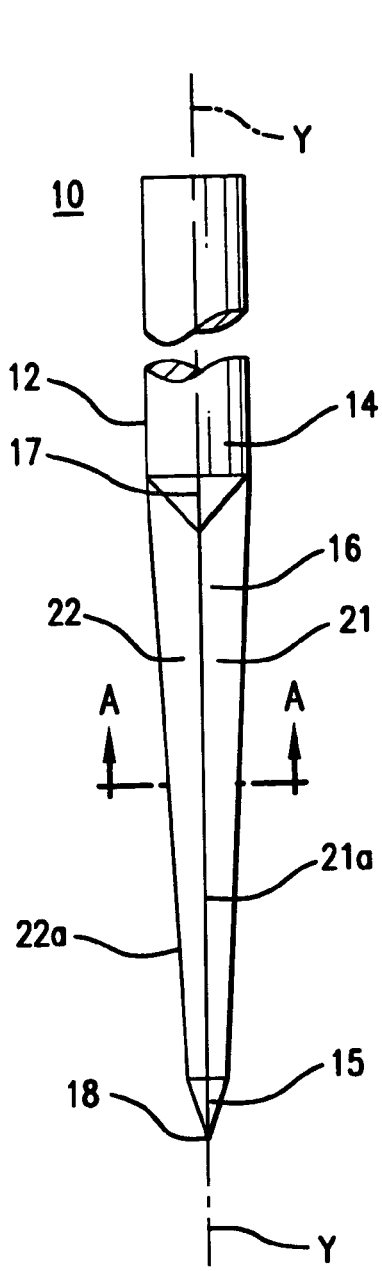
FIG. 1 is a side elevational view of one embodiment of an endodontic instrument according to the present invention.

FIG. 1 illustrates an embodiment of the endodontic instrument 10 in accordance with the present invention. The instrument 10 generally comprises a shaft 12 having a shank portion 14 and an elongated working portion 16. The working portion 16 extends from a proximal end 17 adjacent the base of the shank 14 to a distal end 18 terminating in a tip 15. The shank 14 may include an optional fitting portion (not shown) for mating with the chuck of a dental hand piece (not shown). Alternatively, or in addition to a fitting portion, the shank portion 14 may include a knurled or otherwise treated surface (not shown) or handle to facilitate hand manipulation of the file 10. The endodontic instruments described herein may be used by finger manipulation, or the instruments may be engine driven by attaching the shank portion of the instrument to a motorized hand piece.

Figure 2:
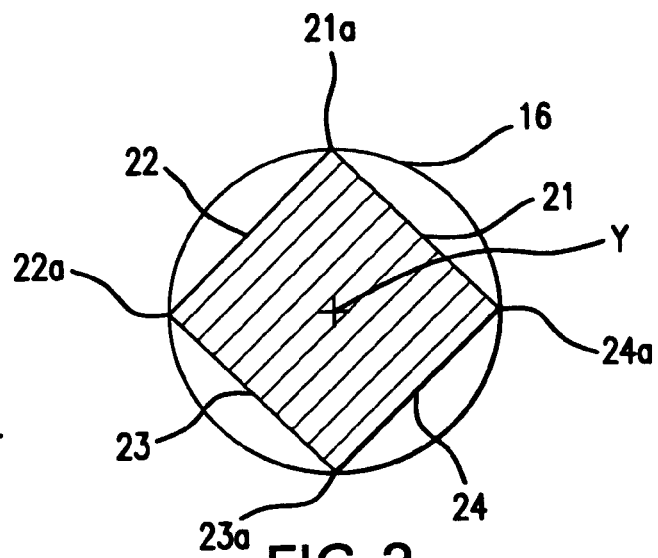
FIG. 2 is an enlarged cross-sectional view of the instrument taken along line A-A of FIG. 1.

As shown in FIGS. 1 and 2, in a preferred embodiment, the endodontic instrument 10 includes four straight flutes 21, 22, 23, and 24 formed in the working portion 16, extending parallel to the central axis Y of the instrument from the distal end 18 adjacent the tip 15 and exiting at the proximal end 17. As shown in FIG. 2, which is a cross-section through working portion 16 of instrument 10, the four flutes 21, 22, 23, and 24 form cutting edges 21a, 22a, 23a, and 24a on the working portion 16. This straight flute concept solves the problem of self-threading of the instrument into the canal because there are no continuous helically oriented cutting edges to dig in and thread or screw into the canal. Those skilled in the art will readily appreciate that a similar instrument could also be configured with one to three straight flutes or five or more flutes, as desired. Furthermore, such flutes can extend either a portion of the length or the entire length of working portion 16.

The flutes can be formed so as to form common geometric cross-sections of working portion 16. Because a straight flute design prevents self-threading, the cross-sectional shape can be made to optimize cutting efficiency and aggressiveness. FIG. 2 shows a square cross-sectional shape of the working portion 16 of instrument 10 containing the flutes 21, 22, 23, and 24 taken along line A-A of FIG. 1. It should be noted that other cross-sectional shapes of the working portion 16 may be utilized with the present invention, the invention not being limited to a particular cross-sectional shape of the peripheral surface. These cross-sectional shapes, which may be symmetrical or asymmetrical, can include, but are not limited to substantially triangular-shaped, substantially trapezoidal-shaped, substantially semi-circular shaped, substantially d-shaped, substantially pie-shaped, and substantially c-shaped. Thus, the working portion 16 of the instrument of the present invention is not limited to a single cross-sectional shape.

Because the shape of the flute space is defined by the cross-section shape of the working portion, flutes 21, 22, 23, and 24 may have the same or different cross-sectional flute shapes. FIG. 2 shows the flute space shape being straight. It should be noted that other flute space shapes may be utilized with the present invention, the invention not being limited to a particular flute space shape. These flute space shapes can include, but are not limited to substantially s-shaped and substantially u-shaped. Thus, the flute space shape is not believed to be critical to the present invention. Furthermore, the flutes can be symmetrically or asymmetrically spaced along the peripheral surface of the working portion.

Figure 3:
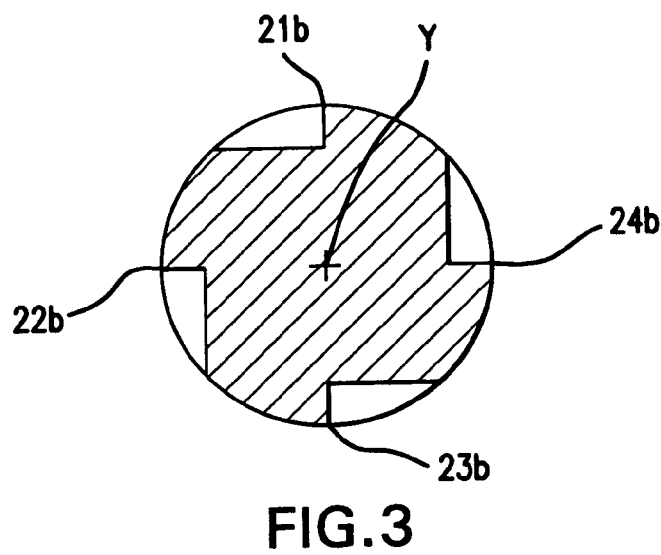
FIG. 3 is another exemplary enlarged cross-sectional view of an endodontic instrument according to the present invention.
Figure 4:
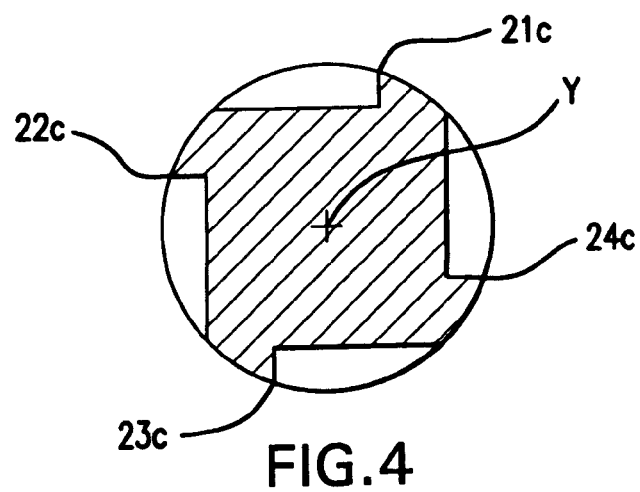
FIG. 4 is another exemplary enlarged cross-sectional view of an endodontic instrument according to the present invention.

The rake angles of the cutting edges 21a, 22a, 23a, and 24a may be positive, negative, or neutral, as desired. FIG. 2 shows an example of the cross-sectional shape of the working portion 16 of instrument 10 taken along line A-A of FIG. 1, where the cutting edges 21a, 22a, 23a, and 24a have a negative rake angle. FIG. 3 shows an example of the cross-sectional shape of the working portion 16 of an instrument having a neutral rake angle of the cutting edges 21b, 22b, 23b, and 24b. FIG. 4 shows an example of the cross-sectional shape of the working portion 16 of an instrument having a positive rake angle of the cutting edges 21c, 22c, 23c, and 24c. It should be noted that other cross-sectional shapes of the working portion 16 may be utilized with the present invention to achieve the desired rake angles, the invention not being limited to a particular cross-sectional shape of the working portion 16. The rake angles of the cutting edges may also be equal to one another or they may be different such that, for example, one may be substantially positive and another may be substantially neutral or negative. The rake angle of one or more cutting edges may also vary along the length of the working portion 16.

In one preferred embodiment, the working portion 16 is uniformly tapered from the proximal end 17 to the distal end 18, as shown in FIG. 1. In other preferred embodiments, the rate of diameter taper may also be nonuniform, meaning that the rate of diameter taper changes along the length of the working portion 16. The tapering of the shaft, in addition to allowing the instrument to be used in the narrow spaces of the canal, further aids in the removal of debris generated by cutting. This is because straight flutes, when cut with the root/base of the flute substantially parallel to the file axis, have a flute space that inherently increases from the distal end 18 to the proximal end 17 of the instrument 10. As debris that is generated during cutting tends to follow the path of least resistance, it will naturally progress from the distal end 18 to the proximal end 17 of the instrument in the direction of the increasing flute space.

Referring to FIG. 5, the cutting edge 21a of flute 21 can be displaced on a shear angle α with respect to central longitudinal axis Y of the instrument 10, where α may range from about 0.1 degrees to about 45 degrees. This displacement further assists in the disbursement of debris up the flute of the instrument 10.

Other improvements well known in the art can be utilized along with the present invention to improve the operating characteristics of the instrument. For example, referring to FIGS. 6 and 7, a helical groove 26 can be formed in a section of the working portion 16 extending from the distal end 18 to the proximal end 17. The helical groove 26 provides notches 27 on the cutting edges 21a, 22a, 23a, and 24a, which relieve the chip load on the cutting edges, 21a, 22a, 23a, and 24a and thus allows the cutting edges 21a, 22a, 23a, and 24a to be more aggressive. Similarly, as shown in FIGS. 8 and 9, one or more circumferential grooves 29 may be formed in the working portion 16 to provide notches 30 on the cutting edges 21a, 22a, 23a, and 24a. The circumferential grooves can be evenly or unevenly spaced along the working portion from the distal end 18 to the proximal end 17.

FIGS. 10-13 depict another preferred embodiment of the endodontic instrument. In this embodiment, the endodontic instrument 210 comprises one flute 221 extending along a portion of the working portion 216 disposed about the central longitudinal axis Y of the instrument, as shown in FIG. 10. The flute 221 comprises three equal length straight flute sections 232, 234, and 236, each being substantially one-third of the total flute length 260. Straight flute section 234 is disposed between straight flute sections 232 and 236. Straight flute sections 232, 234, and 236 are each angularly displaced 120° apart from each other relative to central axis Y. FIGS. 11, 12, and 13 show the cross-sectional views of the working portion 216 for straight flute sections 232, 234, and 236, taken along lines B-B, C-C, and D-D, respectively, in FIG. 10. Those skilled in the art will readily appreciate that a similar instrument could also be configured with two straight flute sections or four or more straight flute sections, as desired, and the length of the straight flute sections could be of the same or of differing lengths. Furthermore, the straight flute sections could be angularly displaced at any desirable consistent or varying angle in relation to each other.

As seen in FIG. 10, straight flute section 232 has a first end 238 and second end 240. Straight flute section 234 has a first end 242 and second end 244, and straight flute section 236 has a first end 246 and a second end 248. In a preferred embodiment, as shown in FIG. 10, there is an intermediate section 250 between the ends of portion 234 and the adjacent ends of 232 and 236. The intermediate section 250, with its greater cross-sectional area, increases the overall strength of the instrument 10, helping to prevent the breakage of the instrument 10 during use.

In another preferred embodiment, the three straight flute sections 232, 234 and 236 may be substantially adjacent to each other. In yet another preferred embodiment, as shown in FIG. 14, the three straight flute sections 232, 234 and 236 may overlap each other. The ends 242 and 244 of straight flute section 234 can also be between the first and second ends of straight flute section 232 and 236. The overlapping of straight flute sections 232 and 234 results in gate 252, which provides a path for the debris to further facilitate debris disbursal up the flute 260.

As shown in FIG. 10, the straight flute sections 232, 234, 236 each comprise first and second end surfaces 254 and 256 with an intermediate surface 258 disposed therebetween. The end surfaces 254 and 256 are each disposed in a plane transverse to the intermediate surface 258. The end surfaces 254 and 256 can be disposed at an angle θ relative to the intermediate surface 258, where θ is greater than or equal to 90°. The angular orientation of θ being greater than 90° (as shown in FIG. 10) further enhances the disbursal of the debris proximally up the flute 260.

Those skilled in the art will appreciate that in alternate embodiments, the flute segments can be shorter in length with less angular displacement between them, e.g., each section spaced 45° from the flute section before it. Other alternative embodiments may also have more than one flute, with each flute being composed of multiple flute sections.

Figure 15:
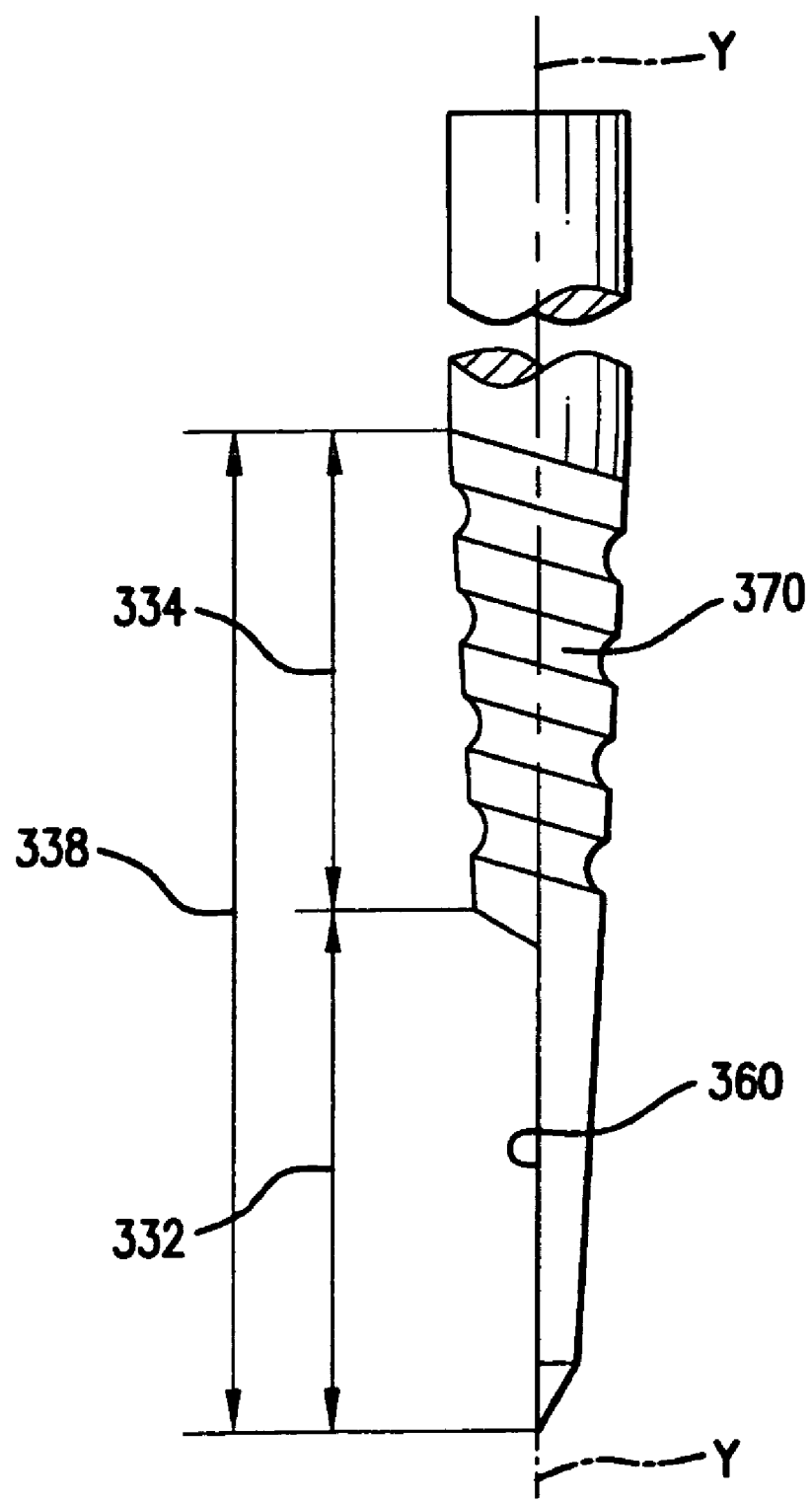
FIG. 15 is a side elevational view of yet another exemplary instrument according to the present invention.
Figure 16:
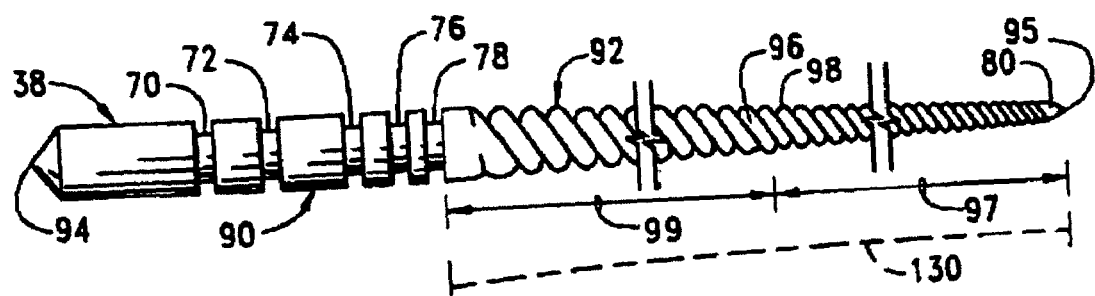
FIG. 16 is a side elevational view of still another exemplary instrument according to the present invention.

FIG. 15 depicts yet another preferred embodiment of an endodontic instrument of the present invention. In this embodiment, two equal length flute segments, 332 and 334 are shown each being one half of the total flute length 338. Flute segment 332 has a straight flute 360, while flute segment 334 has a helical flute 370. Those skilled in the art will readily appreciate that a similar instrument could also be configured with three or more flute segments as desired with at least one segment being a straight flute and another segment being a helical flute. The length of the segments could be the same or various lengths. Furthermore, the segments could be angularly displaced at any desirable consistent or varying angle. FIG. 16 shows still another preferred embodiment of an endodontic instrument 38 having helical flutes 96 according to the present invention.

Figure 17:
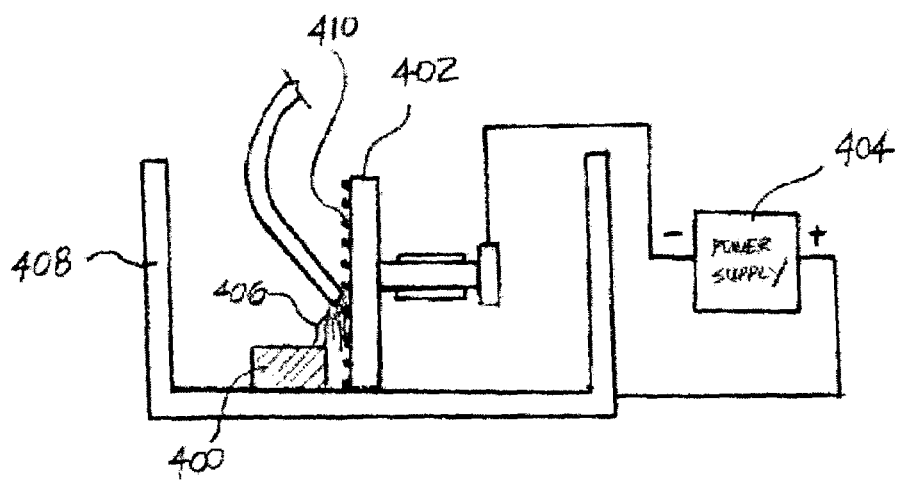
FIG. 17 is a schematic representation of an electrochemical grinding process according to the present invention.

Reference is now made to FIG. 17, which is a schematic representation of an electrochemical grinding process according to the present invention. As shown, the electrically-conductive material blank 400, e.g., nickel titanium, stainless steel, etc., functions as an anode while a special conductive grinding wheel 402 serves as a cathode. A variable power supply 404 supplies current to the apparatus. A continuous stream of electrolyte 406, a conductive aqueous solution consisting of a mixture of chemical salts, such as sodium chloride, and other additives, flows at the interface of the grinding wheel and material blank and passes the electrical current in the circuit. The volume, pressure, content, and concentration of the electrolyte may be controlled and adjusted by an operator. As known in the art, different types of grinding wheels (metal bond, resin bond, etc.), grit types (diamond, aluminum oxide, etc.), and grit sizes may be employed. Grinding wheel speed, surface speed, and material feed rate may also be adjusted and optimized for a given application.

A tank 408 may collect, filters and recycle the electrolyte fluid. At the positive electrode, or anode, oxidation of the material blank 400 dissolves the surface of the metal and forms a metal oxide film. The film is electrically insulating, and acts as a barrier against the electrochemical cutting action of the process. The abrasives 410 in the rotating grinding wheel continually remove this film and expose a fresh surface for oxidation. Metal deposition on the grinding wheel (cathode) is avoided by proper choice of electrolyte virtually eliminating the need for repeated redressing of the surface of the grinding wheel 402 common in traditional grinding processes. The continual dissolution of the surface of the material blank 400 combined with the mechanical removal of surface oxides results in a superior and efficient, heat-free manufacturing process to produce endodontic instruments free of burrs, material stresses and mechanical distortions. The process has been shown to work well on all materials with appropriate conductivity and electrochemical reactivity such as Stainless Steel and Nickel Titanium, which are commonly used for endodontic instruments.

In addition, a modification of this new manufacturing method optimizes the creation of desired ultra-sharp cutting edges (shown as 21*a*, 22*a*, 23*a*, and 24*a* in FIG. 2) at intersecting flute surfaces on endodontic instruments 10. This modification of the process involves the reduction of the current flow to very low levels which minimizes the chemical dissolution activity of the process and enhances the mechanical abrasion in the process during final finish cut passes at very minimal depths of cut. For example, in one variation, the voltage applied is reduced from 6 volts to about 1 volt during the final finishing pass of the grinding wheel. In the extreme of this modification of the process the current flow has been eliminated entirely in the final minimum depth finishing cut.

Endodontic instruments manufactured according to the present invention may be produced by first grinding one or more cutting flutes into the raw material and then grinding the outside diameter and taper of the instrument to the desired size, all in one operation on one machine, or on two or more separate machines. Conversely, the outside diameter and taper could be ground first, followed by the flutes. Again, these processes could all be performed on one machine, or by employing more than one machine. Furthermore, rather than just moving the part past the grinding wheel along one axis of movement, as in current methods of manufacture, the methods used in the present invention may include the movement of the grinding wheel past the part while simultaneously translating the grinding wheel in multiple axes.

In one method of manufacture the raw material can be automatically fed from blank, bar, or coil stock into custom support tooling. In a preferred embodiment the support tooling itself can also be translated in various axes to assure proper support of the instrument as it is being ground. The stock may then be rotated about its longitudinal axis. A form-dressed rotating grinding wheel is then brought into contact with the leading end of the rotating stock to form the tip of the instrument. Next the grinding wheel is retracted to the proper depth, and a retraction and linear feed rate is engaged proportional to the rpm of the rotating stock and the surface speed of the grinding wheel to produce the desired diameter, taper and finish of the tapered diameter of the part. As the tapered part feeds past the grinding wheel, it travels into the tapered support section of the work support. After the tapered portion is completed, a second grinding wheel with appropriate form is properly oriented above the supported tapered part, and then fed into the stationary tapered part to produce the desired flute form and depth. The grinding wheel is then retracted and the tapered part is repositioned radially and/or axially so that it is properly oriented for the next flute to be ground. This process is repeated until all the desired flutes are ground. Finally, the completed part is parted off at the same time as the point the next part is established.

The embodiments disclosed herein are illustrative and exemplary in nature and it will be appreciated that numerous modifications and other embodiments of the instrument disclosed may be devised by those skilled in the art. Therefore, it will be understood that the appended claims are intended to cover all such modifications and embodiments which come within the spirit and scope of the present invention.

What is claimed is:

1. A method of manufacturing an endodontic instrument comprising the steps of:
    (a) forming an instrument blank from stock material;
    (b) applying an electric current between an electrically conductive grinding wheel, acting as a cathode, and the instrument blank, acting as an anode;
    (c) applying a stream of electrolyte fluid at an interface between the grinding wheel and the instrument blank, the electrolyte fluid having an associated volume and pressure;
    (d) advancing the instrument blank past the electrically conductive grinding wheel to remove material from the instrument blank to form at least one cutting flute;
    (e) reducing the electric current applied between the grinding wheel and the instrument blank; and
    (f) advancing the instrument blank past the electrically conductive grinding wheel to remove material from the instrument blank to form a finish surface on the at least one cutting flute.

2. The method of claim 1, wherein the instrument blank is formed of an electrically conductive material.

3. The method of claim 2, wherein the instrument blank is formed of nickel titanium.

4. The method of claim 2, wherein the instrument blank is formed of stainless steel.

5. The method of claim 1, wherein in step (e), the electric current is eliminated entirely.

6. The method of claim 1, wherein in step (c), the volume of electrolyte fluid is varied.

7. The method of claim 1, wherein in step (c), the pressure of electrolyte fluid is varied.

8. The method of claim 1, wherein in step (c), the electrolyte fluid includes a salt.

9. The method of claim 8, wherein in step (c), the salt has an associated concentration, and the concentration of the salt is varied.

10. The method of claim 8, wherein the salt is sodium chloride.

11. The method of claim 1, further comprising the steps of:
    (g) rotating the instrument blank; and
    (h) repeating steps (b) through (f) to form a plurality of cutting flutes on the instrument blank.

12. The method of claim 1, wherein the at least one cutting flute is helically-shaped.

13. The method of claim 1, wherein the at least one cutting flute is substantially straight.

14. The method of claim 1, wherein step (d) further includes removing material from the instrument blank to form a taper.

15. The method of claim 1, wherein the method utilizes a combination of electrical energy, chemical energy and mechanical abrasion to form flutes in the instrument blank.

16. The method of claim 1, wherein the method does not impact any mechanical properties, such as hardness, of the instrument blank.

17. The method of claim 1, wherein the grinding wheel removes metal oxide film formed on a surface of the instrument blank to expose a fresh surface for oxidation.

18. A method of manufacturing an endodontic instrument comprising the steps of:
    (a) forming an instrument blank from stock material;
    (b) applying an electric current between an electrically conductive grinding wheel, acting as a cathode, and the instrument blank, acting as an anode;
    (c) applying a stream of electrolyte fluid at an interface between the grinding wheel and the instrument blank, the electrolyte fluid having an associated volume and pressure;

(d) rotating the instrument blank as it advances past the electrically conductive grinding wheel to remove material from the instrument blank to form at least one cutting flute having a helical shape;

(e) reducing the electric current applied between the grinding wheel and the instrument blank; and (f) rotating the instrument blank as it advances past the electrically conductive grinding wheel to remove material from the instrument blank to form a finish surface on the at least one cutting flute.

19. The method of claim 18, wherein the instrument blank is formed of an electrically conductive material.

20. The method of claim 19, wherein the instrument blank is formed of nickel titanium.

21. The method of claim 19, wherein the instrument blank is formed of stainless steel.

22. The method of claim 18, wherein in step (e), the electric current is eliminated entirely.

23. The method of claim 18, wherein in step (c), the volume of electrolyte fluid is varied.

24. The method of claim 18, wherein in step (c), the pressure of electrolyte fluid is varied.

25. The method of claim 18, wherein in step (c), the electrolyte fluid includes a salt.

26. The method of claim 25, wherein in step (c), the salt has an associated concentration, and the concentration is varied.

27. The method of claim 26, wherein the salt is sodium chloride.

28. The method of claim 18, further comprising the steps of:

(g) rotating the instrument blank; and (h) repeating steps (b) through (f) to form a plurality of cutting flutes on the instrument blank.

29. An endodontic instrument comprising at least one cutting flute, the cutting flute formed by the steps of:

(a) applying an electric current between an electrically conductive grinding wheel, acting as a cathode, and an instrument blank, acting as an anode;

(b) applying a stream of electrolyte fluid at an interface between the grinding wheel and the instrument blank, the electrolyte fluid having an associated volume and pressure;

(c) advancing the instrument blank past the electrically conductive grinding wheel to remove material from the instrument blank to form the at least one cutting flute;

(d) reducing the electric current applied between the grinding wheel and the instrument blank; and (e) advancing the instrument blank past the electrically conductive grinding wheel to remove material from the instrument blank to form a finish surface on the at least one cutting flute.

30. The endodontic instrument of claim 29, wherein the instrument blank is formed of an electrically conductive material.

31. The endodontic instrument of claim 30, wherein the instrument blank is formed of nickel titanium.

32. The endodontic instrument of claim 30, wherein the instrument blank is formed of stainless steel.

33. The endodontic instrument of claim 29, wherein in step (e), the electric current is eliminated entirely.

34. The endodontic instrument of claim 29, wherein in step (c), the volume of electrolyte fluid is varied.

35. The endodontic instrument of claim 29, wherein in step (c), the pressure of electrolyte fluid is varied.

36. The endodontic instrument of claim 29, wherein in step (c), the electrolyte fluid includes a salt.

37. The endodontic instrument of claim 36, wherein in step (c), the salt has an associated concentration, and the concentration of the salt is varied.

38. The endodontic instrument of claim 29, further comprising a plurality of cutting flutes.

39. The endodontic instrument of claim 29, wherein the at least one cutting flute is helically-shaped.

40. The endodontic instrument of claim 29, wherein the at least one cutting flute is substantially straight.

41. The endodontic instrument of claim 29, wherein the instrument is tapered.

* * * * *